United States Patent [19]

Kaneta et al.

[11] Patent Number: 4,803,884

[45] Date of Patent: Feb. 14, 1989

[54] METHOD FOR MEASURING LATTICE DEFECTS IN SEMICONDUCTOR

[75] Inventors: Hiroshi Kaneta, Kawasaki; Tsutomu Ogawa, Machida; Haruhisa Mori, Yokohama; Kunihiko Wada, Kawasaki, all of Japan

[73] Assignee: Fujitsu Limited, Kawasaki, Japan

[21] Appl. No.: 136,691

[22] Filed: Dec. 22, 1987

[30] Foreign Application Priority Data

Dec. 26, 1986 [JP] Japan .................................. 61-314984

[51] Int. Cl.$^4$ ............................................. G01N 29/04
[52] U.S. Cl. ........................................ 73/598; 73/597; 374/117
[58] Field of Search ................. 73/598, 597, 571, 591, 73/587, 584, 570, 618, 601; 324/158 R; 374/5, 6, 117

[56] References Cited

U.S. PATENT DOCUMENTS

| | | | |
|---|---|---|---|
| 4,342,518 | 8/1982 | Shirley | 73/597 |
| 4,366,713 | 1/1983 | Gilmore et al. | 73/618 |
| 4,621,233 | 11/1986 | Davari et al. | 324/158 R |

Primary Examiner—Stewart J. Levy
Assistant Examiner—Louis M. Arana
Attorney, Agent, or Firm—Staas & Halsey

[57] ABSTRACT

A method for measuring lattice defects in semiconductor such as a silicon crystal, detects an ultrasonic velocity of an ultrasonic pulse propagating through the semiconductor to which heat is variably applied. An elastic constant of the semiconductor is calculated from the ultrasonic velocity, and a concentration or density of lattice defects of the semiconductor is obtained by converting the elastic constant.

11 Claims, 3 Drawing Sheets

METHOD FOR MEASURING LATTICE DEFECTS IN SEMICONDUCTOR

BACKGROUND OF THE INVENTION

1. Field of the Invention

The present invention generally relates to a method for measuring lattice defects in a semiconductor, and in particular, to a method for measuring a concentration or density of lattice defects producing low energy unharmonic excitation. The present invention more specifically relates to a method for measuring a concentration or density of interstitial oxygen impurity and/or crystal defects relating to the interstitial oxygen impurity in silicon crystal.

2. Description of the Related Art

As is well known, silicon crystals are widely used for substrates of semiconductor devices such as a very large scale integrated circuit (VLSI). In general, a silicon crystal is required to be as pure as possible. That is, it is desired that the silicon crystal has very few lattice defects. In contrast, there are some cases where lattice defects are positively utilized for particular applications. Useful lattice defects depend on the type of impurities or crystal defects. For example, interstitial oxygen impurity and/or crystal defects relating to the interstitial oxygen impurity (initially precipitated nuclei) are a typical example. The interstitial oxygen impurity and/or the related defects are precipitated and/or grown by a heat treatment process. The precipitation of the interstitial oxygen impurity and/or the related crystal defects are useful for intrinsic gettering (frequently abbreviated as IG), in which the interstitial oxygen impurity and/or the related crystal defects have a function of attracting heavy metal impurities upon fabricating the silicon devices. In the intrinsic gettering process, it is necessary to suitably define the concentration (density) of the interstitial oxygen impurity and/or the related crystal defects and to optimize the corresponding process conditions. Also, it is necessary to precisely validate the concentration of the interstitial oxygen impurity and/or the related crystal defects upon producing silicon crystal or for the quality control of the produced silicon crystal. For these reasons, it is important to measure and know the concentration of the interstitial oxygen impurity and/or the related crystal defects.

Conventionally, the concentration of interstitial oxygen impurity in a silicon crystal, which is one of the lattice defects, is measured by means of an optical measurement such as an infrared absorption method or a far infrared absorption method. These methods utilize a physical phenomenon that the interstitial oxygen impurity causes absorption of intrinsic wavelengths. Therefore, the concentration of the interstitial oxygen impurity is obtainable by the proportional conversion of the intensity of the absorption measured.

Of the absorbed wavelengths intrinsic to the interstitial oxygen impurity in the silicon crystal, an absorption band of a wavelength of 1106 cm$^{-1}$ is widely used for the infrared absorption method. At a lower temperature equal to or less than 20° K, an intrinsic absorption in the far infrared band (25–60 m$^{-1}$) is available. The accuracy of the far infrared absorption method is thus better than that of the infrared absorption method.

However, with the optical measuring methods described above it gradually becomes more difficult to measure the intensity of the absorbed wavelength, as the concentration of dopants (P, B, As, Sb or the like) included in the silicon crystal increases. In the case in which the silicon crystal is in a lower resistivity range of 0.05–0.005 Ω·cm (i.e., heavily doped over 0.3 ppm), which is useful for practical use, it is impossible to measure the absorption intensity due to the interstitial oxygen impurity in the heavily doped silicon crystal at not only room temperature but also low temperature. In addition, it is currently impossible to detect crystal defects such as an initially precipitated nuclei relating to the interstitial oxygen impurity. Reasons for the disadvantages of the conventional optical measurement are as follows.

In the case of infrared absorption at room temperature, the strong absorption due to many free carriers caused by the abundant dopants, or the dopants of high concentration, conceals the intrinsic absorption of the interstitial oxygen impurity and/or the related crystal defects. In the case of infrared absorption at a lower temperature (substantially equal to a temperature of liquid helium), there exist many neutral donors and acceptors caused by the abundant dopants. Strong absorption, which occurs when these donors and acceptors are ionized, conceals the intrinsic absorption of the interstitial oxygen impurity and/or the related crystal defects.

In the case of far infrared absorption at room temperature, each of the vibrational quantum levels of oxygen impurity is uniformly excited by the application of heat, independent of the concentration of dopants. Accordingly, the induced absorption and emission are substantially equal to each other, and therefore, no real absorption occurs. In the case of far infrared absorption at a lower temperature, the impurity levels of the dopants form bands resulting from the abundant dopants. Then, the strong far infrared absorption due to the intra-band optical transition in the impurity band conceals the intrinsic far infrared absorption of the interstitial oxygen impurity and/or the related crystal defects.

Also, conventional measuring methods other than optical measuring methods are known for especially determining the concentration of the interstitial oxygen impurity and/or the related crystal defects in the highly doped silicon crystal. Examples of these are (i) a secondary ion mass spectroscopy (generally abbreviated as SIMS), (ii) a radio activation analysis and (iii) a method for carrying out the infrared absorption measuring method after compensating the acceptors by injecting a high energy electron beam.

However, in methods (i) and (ii), all of the oxygen atoms included in the silicon crystal are simply detected as a whole, irrespective of conditions of the oxygen atoms. Therefore, it is impossible to discriminate the interstitial oxygen impurity and/or the related crystal defects from other oxygen atoms and to determine the concentration or density. It should be noted that the interstitial oxygen impurity and/or the related crystal are the most important factors for producing semiconductor devices.

The above method (iii) can discriminate the interstitial oxygen impurity and/or the related crystal defects from other defects. However, there is a possibility that the projection of the high energy electron beam changes the conditions of silicon crystal subject to the measurement. In this regard, method (iii) may be said to be a kind of destructive measurement. In addition, method (iii) is effective only for p-type crystals. Moreover, the measuring work is cumbersome.

SUMMARY OF THE INVENTION

Accordingly, a general object of the present invention is to provide a novel and useful method for measuring lattice defects in a semiconductor in which the above disadvantages have been eliminated.

A more specific object of the present invention is to provide a method for measuring lattice defects in a semiconductor capable of measuring the concentration (density) of the interstitial oxygen impurity and/or the crystal defects relating to the interstitial impurity oxygen, even when the concentration of dopants doped in the semiconductor is high.

The above object of the present invention is accomplished by a method for measuring lattice defects in a semiconductor comprising the steps of applying an ultrasonic pulse to the semiconductor; detecting temperature of the semiconductor to which heat is applied; detecting the ultrasonic pulse passed through the semiconductor; and measuring the relative change of ultrasonic velocity of the detected ultrasonic pulse passed through the semiconductor at the detected temperature to obtain an elastic constant of the semiconductor corresponding to the ultrasonic velocity. A concentration or density of lattice defects producing low energy unharmonic excitation is converted from the elastic constant.

Other objects and features of the present invention will become apparent from the following detailed description when read in conjunction with the accompanying drawings.

DETAILED DESCRIPTION OF THE PREFERRED EMBODIMENTS

The present invention utilizes the following physical law which has been recently proposed. That is, in a case where there exist low energy quantum levels (low energy excitation) which are unharmonic and sensitive to a pressure (lattice strain), an elastic constant of a crystal reveals anomalous change in temperature region near an absolute temperature substantially corresponding to a ratio $\Delta/k$ of an energy level separation $\Delta$ between the above low energy quantum levels to the Boltzmann's constant k, as compared with a crystal having no unharmonic low energy quantum level.

The inventors of the present invention found that the above physical law is applicable to a semiconductor including lattice defects producing the unharmonic excitation and created the present invention described in detail below.

That is, one of essential features of the present invention is that the measurement of the concentration or density of lattice defects producing the unharmonic excitation in a semiconductor is carried out by measuring an elastic constant of the semiconductor and converting the measured elastic constant into the concentration or density of the lattice defects.

Presently, a few examples of the above-described elastic anomaly in a crystal system having impurities (i.e., the anomalous temperature dependence relative to the normal one in a crystal having no impurity) have been reported. It should be noted, however, that the reported elastic anomaly is substantially based on ionic crystal or small impurities as hydrogen included in metal. The reported elastic anomaly in the impurity crystal depends on the following physical phenomenon. That is, in large vacant spaces in a host crystal (spaces between host crystal ions in the case of the substitutional impurities), there exist the impurities of relatively small atomic (or ionic) radii which are loosely bound. Therefore, the impurity atoms move in the impurity crystal in accordance with the tunneling motion in which the atoms hop through many stable positions or in accordance with the unharmonic motion in which the atoms move in a wider movable region. These motions of the impurity atoms cause the low energy excitation which is closely related to the elastic anomaly.

One example of the behavior of the impurity atoms is explained with reference to FIG. 1.

Figure 1:
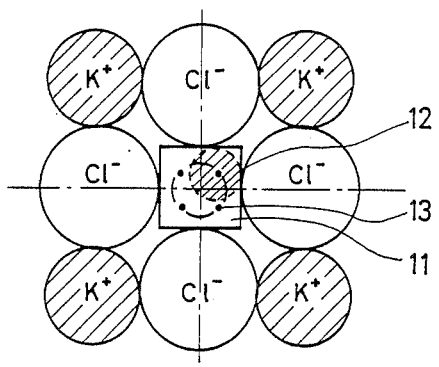
FIG. 1 is a schematic view for explaining motion of an impurity atom Li in KCl:Li of an ionic crystal impurity system.

FIG. 1 is a schematic view showing the motion of an impurity atom Li in KCl:Li which is one of the ionic crystal systems. As can be seen, a Li$^+$ ion 12 of the substitutional impurity is loosely bound into a vacant space 11 surrounded by K$^+$ ions shown by hatched circles. The Li$^+$ ion 12 moves by tunneling through many stable positions 13 represented by small black circles in the gap 11.

On the other hand, with regard to the lattice defects producing the unharmonic excitation in the semiconductor, the interstitial oxygen impurity in a silicon (Si) crystal is known.

Figure 2:
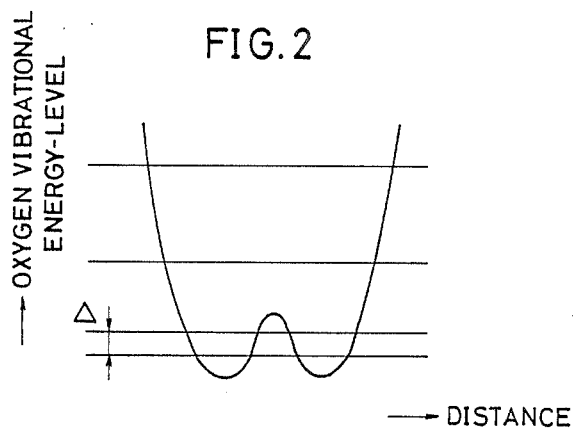
FIG. 2 is a graph showing a low energy quantum level due to unharmonic vibration of interstitial oxygen impurity in silicon crystal.

The quantum energy level due to the unharmonic vibration of the interstitial oxygen impurity is shown in FIG. 2. The horizontal axis represents a distance between atoms and the vertical axis represents an energy level. A curved line is a characteristic line of the unharmonic potential for interstitial impurity oxygen. A symbol $\Delta$ denotes an energy gap between low energy quantum levels. It should be noted that the physical phenomenon causing the low energy excitation due to the interstitial oxygen impurity is considerably different from that in the above mentioned ionic impurity crystals, as described below.

That is, it cannot be said that the above-described physical phenomenon that the oxygen impurity atoms are loosely bound in the host crystal cannot be applied to the silicon crystal, because the oxygen impurity atoms producing the unharmonic excitation are the interstitial type. In addition, it cannot be said that the atomic radius in the covalent bond of the oxygen impurity atom with respect to adjacent silicon atoms is considerably small. It is proper to say that the oxygen impurity is positioned at an intermediate portion of the Si—Si covalent bond axis, which is the smallest gap in the host crystal.

Figure 3:
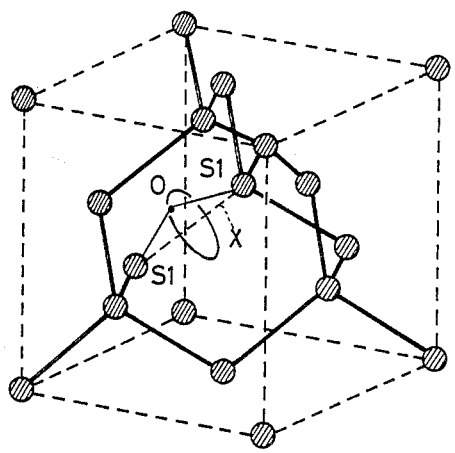
FIG. 3 is a schematic view for explaining motion of interstitial oxygen impurity in silicon crystal including interstitial oxygen impurity atoms.

However, the oxygen impurity forms the covalent bonds together with two silicon atoms located on both sides thereof. Thus, a delicate balance between an attracting force and a repulsive force of the inter atomic potential or a kind of the quasi Jahn-Teller effect exists. In this case, the repulsive force is slightly superior to the attracting force. Therefore, the oxygen impurity becomes located at an off-center position slightly away from the original Si—Si covalent binding axis. As a result, as shown in FIG. 3, the interstitial oxygen impurity presents the unharmonic vibrational motion including the rotational motion around a covalent binding axis.

That is, it can be said that in the case of the interstitial oxygen impurity in the silicon crystal, the occurrence of the low energy excitation or its physical behavior could not be anticipated from the consideration of the above-described ionic crystal or the impurities in metal. Actually, the low energy excitation is clearly distinct between the ionic crystal and metal systems and the silicon crystal. For example, the energy-level spacing $\Delta$ between the quantum levels in the ionic crystal system or the metal system is approximately 0.1-0.3 meV. On the other hand, the energy gap between the quantum levels of the interstitial oxygen impurity in the silicon crystal (FIG. 2) is one order greater than the former case.

Nevertheless, the inventors of the present invention found that the physical law described previously is applicable to the interstitial oxygen impurity in the silicon crystal. In addition, the physical law is also applicable to crystal defects relating to the oxygen impurity producing the unharmonic vibration. The related crystal defects either occur together with the interstitial oxygen impurity or independently thereof. A result of an experiment conducted by the present inventors revealed that a temperature dependence of the elastic constant differs greatly between the silicon crystal having the interstitial oxygen impurity and the silicon crystal having no interstitial impurity oxygen. This experimental result described in detail later supports the above-described theoretical consideration regarding the oxygen impurity and/or the related crystal defects in the silicon crystal.

The low energy quantum level resulting from the rotational unharmonic vibration of the interstitial oxygen impurity in the silicon crystal is approximately $\Delta \sim 4$ meV and therefore shows a sensitive pressure dependency. Therefore, the present invention is intended to measure an acoustic velocity of an ultrasonic wave penetrating through the silicon crystal and obtain the elastic constant thereof.

A description will be given on an apparatus for implementing the measuring method of the present invention.

Figure 4:
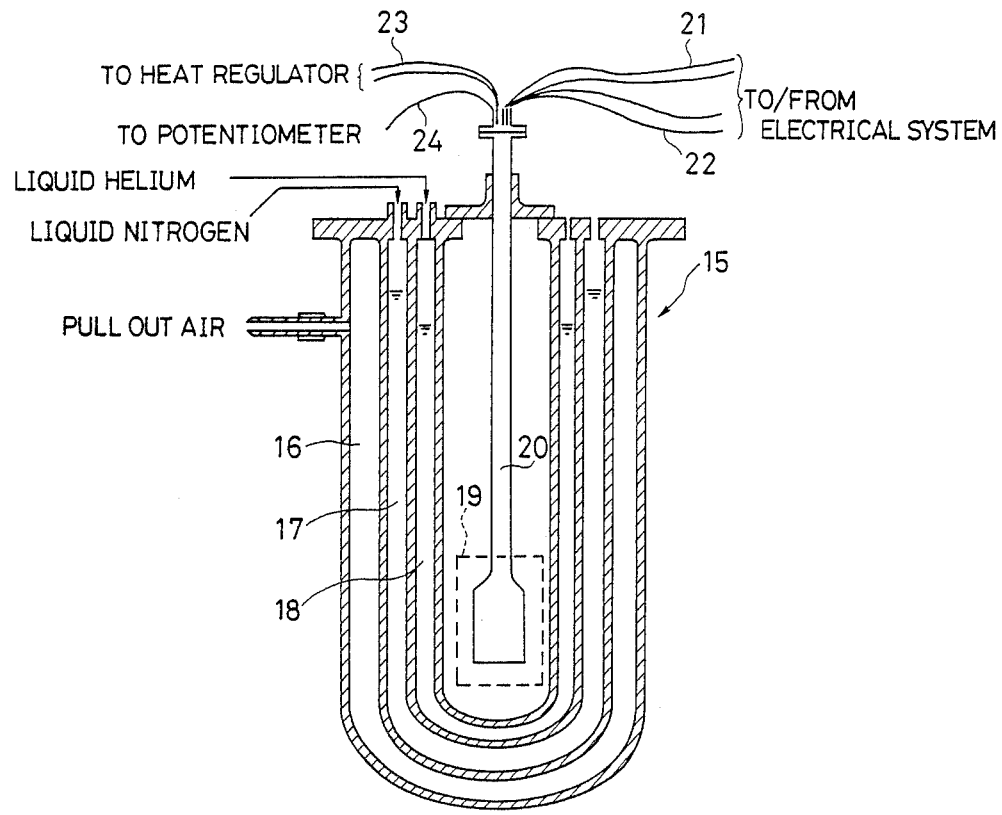
FIG. 4 is a sectional view of a low temperature cryostat used upon implementing the method of the present invention.

FIG. 4 is a sectional view of a low temperature cryostat. A cryostat 15 has three baths 16, 17 and 18. The first baths 16 is a vacuum heat insulating bath at a pressure of approximately $10^{-4}$ torr at maximum. The second bath 17 is a coolant bath in which liquid nitrogen is sealed. The third bath 18 is a coolant bath in which a liquid helium is sealed.

A measuring rod 20 having a sample room 19 positioned at a extreme end thereof is inserted into an central part inside the low temperature cryostat 15. To the other extreme end of the cryostat 15, there are attached wires 21 and 22 extending to an electrical system for generating and detecting an ultrasonic pulse signal, wires 23 extending to a heat regulator (not shown) for regulating a temperature of the sample room 19, and a code 24 connected to a potentiometer at one end thereof and a thermocouple at the other end.

Figure 5:
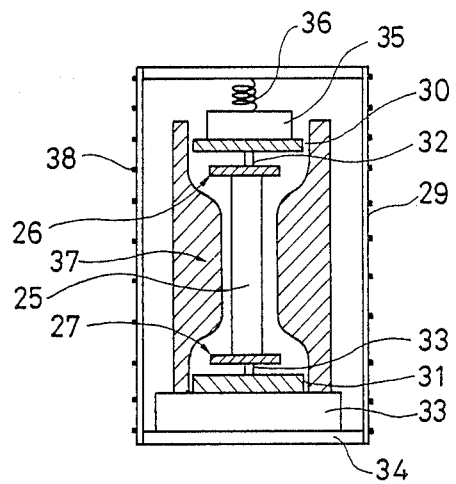
FIG. 5 is a sectional view showing an inner part of a sample room shown in FIG. 4.

A section of an inner part of the sample room 19 is constituted as shown in FIG. 5. In the inner part of the sample room 19, there is provided a sample 25 of a silicon crystal (5 mm×5 mm of a rectangular cross section, 15 mm in length). Ultrasonic pulse transducers 26 and 27 using piezo material are attached to the top and bottom ends of the sample 25, respectively. The ultrasonic pulse transducers 26 and 27 are supported and electrically connected to electrodes 30 and 31 by means of brass rods 32 and 33, respectively. The wires 21 and 22 shown in FIG. 4 are electrically connected to the electrodes 30 and 31, respectively. The electrode 31 is supported on a base plate 33 mounted on a bottom plate 34, and the electrode 30 is supported on a base plate 35 which is urged by a coil spring 36. A metallic holder 37 surrounds the sample 25 to make the temperature distribution over the sample 25 uniform. The holder 37 is not necessarily needed. The thermocouple (not shown) for detecting temperature variations of the sample 25 is attached to the metallic holder 37. The thermocouple is electrically connected to the code 24 shown in FIG. 4. A resistance thermometer may be used together with or instead of the thermocouple. The above elements are accommodated in a hollow cylindrical solenoid 29. A heater wire 38 electrically connected to the heat regulator (not shown) by the wires 23 is wound around the solenoid 29.

The lowest temperature available in the measuring system described above is around 6° K when the cooling medium bath 18 is not kept in a vacuum. When the bath 18 is made to have a vacuum, the lowest temperature of about 2° K is available. The frequency of the ultrasonic pulse may be set in the range of 100 kHz to 1 GHz.

An experimental result by use of the measuring system described above is described below. In the experiment, a silicon crystal including the interstitial oxygen impurity of approximately 30 ppm was used as the sample 25. The frequency of the ultrasonic pulse was set to 10 MHz. Heat was variably applied to the sample 25. Under these conditions, ultrasonic pulses were applied to the sample 25 through the transducer 26 and detected by the transducer 27 positioned opposite the transducer 26. Then, the ultrasonic velocity propagating through the sample 25 was measured as a function of the temperature thereof. The relative change of the elastic constant of silicon crystal $((c_{11}-c_{12})/2)$ was measured in the temperature range of 100° K-2° K.

Figure 6:
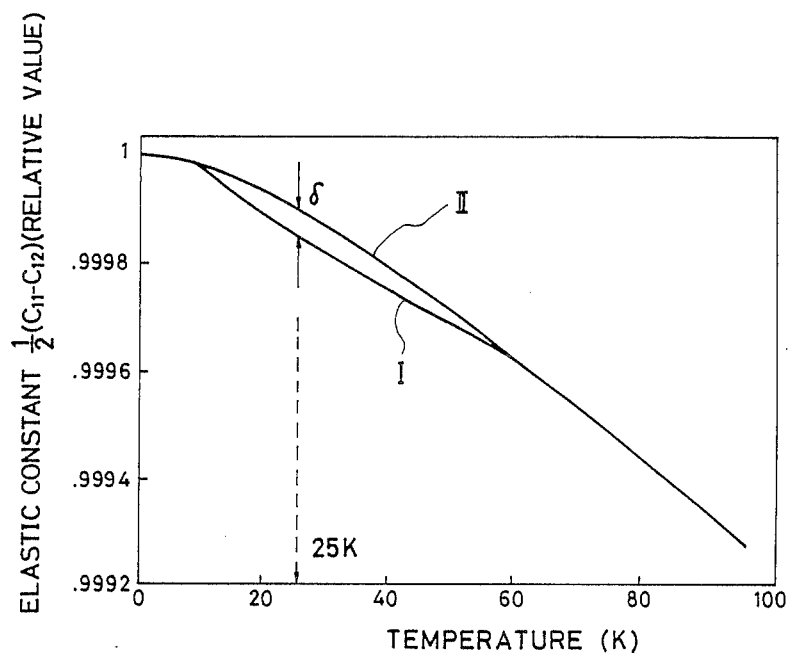
FIG. 6 is an elastic constant versus temperature for explaining an experimental result based on the present invention.

An experimental result is shown by a curved line I in FIG. 6 which shows a temperature versus elastic constant characteristic. In this figure, the elastic constant is represented as a relative value, in which an elastic constant at a temperature of 4° K is defined as "1".

A curved line II is a characteristic line of a silicon crystal including no interstitial oxygen impurity or the related crystal defects. According to the physical law described above, the temperature $\Delta/k$ of silicon crystal is approximately 25° K. As clearly shown in FIG. 6, the elastic constant of the silicon crystal including the interstitial oxygen impurity shows an abnormal variation at a temperature of around 25° K, as compared with the silicon crystal having no interstitial impurity oxygen. An amount $\delta$ (relative value) of the abnormal variation in the elastic constant (or ultrasonic velocity) is of the order of $10^{-4}$. On the other hand, a relative accuracy of the measurement of the ultrasonic velocity in the measuring system may be 3; ensured to be on the order of $10^{-6}$. As a result, measurements by the method of the present invention can be made with a level of confidence to about two decimal places, and is therefore reliable.

Generally speaking, it may be said that the concentration (density) of the interstitial oxygen impurity and/or the related crystal defects is substantially proportional to the amount δ of the abnormal variation in elastic constant (or ultrasonic velocity). Therefore, it is possible to obtain the concentration of the interstitial oxygen impurity and/or related crystal defects by measuring the amount δ of the abnormal variation in elastic constant.

As discussed in the foregoing, the present invention makes it possible to obtain the concentration of the interstitial oxygen impurity and/or the related crystal defects in the deeply doped silicon crystal (including donors or acceptors of 0.1 ppm or over) by use of an ultrasonic pulse. It should be appreciated that the present invention measures the concentration of the interstitial oxygen impurity and/or related crystal defects without destroying the crystal. Moreover, the present invention is applicable to not only a p-type semiconductor but also an n-type semiconductor.

The present invention is not limited to the embodiments described above, and numerous variations and modifications may be made without departing from the scope of the present invention. For example, the present invention is applicable to semiconductors other than silicon crystal such as GaAs.

What is claimed is:

1. A method for measuring lattice defects in a semiconductor crystal, comprising the steps of:
    applying an ultrasonic pulse to said semiconductor crystal;
    setting said semiconductor crystal at a predetermined temperature;
    detecting said ultrasonic pulse passed through said semiconductor crystal;
    measuring an ultrasonic velocity of said detected ultrasonic pulse passed through said semiconductor crystal with respect to said predetermined temperature to obtain an elastic constant of said semiconductor crystal corresponding to said ultrasonic velocity; and
    determining a difference between the elastic constant of the semiconductor crystal and an elastic constant of a semiconductor crystal known to have no lattice defects at the same predetermined temperature, said difference correlating to a concentration or density of lattice defects producing low energy unharmonic excitation.

2. A method for measuring lattice defects in a semiconductor crystal as claimed in claim 1, wherein said semiconductor crystal is a silicon crystal.

3. A method for measuring lattice defects in a semiconductor crystal as claimed in claim 1, wherein said lattice defects are interstitial oxygen impurity and crystal defects relating to said interstitial oxygen impurity of said semiconductor crystal.

4. A method for measuring lattice defects in a semiconductor crystal as claimed in claim 1, wherein said semiconductor crystal is silicon crystal including donor impurity of 0.1 ppm or over.

5. A method for measuring lattice defects in a semiconductor crystal as claimed in claim 1, wherein said semiconductor crystal is silicon crystal including acceptor impurity of 0.1 ppm or over.

6. A method for measuring lattice defects in a semiconductor crystal as claimed in claim 1, wherein said temperature of said semiconductor crystal is set to a temperature of 150° K or below.

7. A method for measuring lattice defects in a semiconductor crystal as claimed in claim 1, wherein a frequency of said ultrasonic pulse is in the range of 100 kHz to 1 GHz.

8. A method for measuring lattice defects in a semiconductor crystal as claimed in claim 1, wherein said concentration or density of said lattice defects is proportionally derived from said difference in elastic constant.

9. A method for measuring lattice defects in a semiconductor crystal as claimed in claim 1, wherein said temperature of said semiconductor crystal is detected by use of a thermocouple.

10. A method for measuring lattice defects in a semiconductor crystal as claimed in claim 1, wherein said temperature of said semiconductor crystal is detected by use of a resistance thermometer.

11. A method for measuring lattice defects in a semiconductor crystal as claimed in claim 1, wherein said applying and detecting steps comprise applying an ultrasonic pulse with a transmitting ultrasonic transducer and detecting said ultrasonic pulse with a receiving ultrasonic transducer.

* * * * *

UNITED STATES PATENT AND TRADEMARK OFFICE
CERTIFICATE OF CORRECTION

PATENT NO. : 4,803,884
DATED : February 14, 1989
INVENTOR(S) : HIROSHI KANETA et al.

It is certified that error appears in the above-identified patent and that said Letters Patent is hereby corrected as shown below:

[54] after "IN" insert --A--;

Col. 5, line 63, "a" should be --an--;
and "an" should be --a--;

Col. 7, line 2, delete "3;";

Col. 8, line 12, "of" should be --in--.

Signed and Sealed this

Twenty-fifth Day of July, 1989

Attest:

DONALD J. QUIGG

Attesting Officer

Commissioner of Patents and Trademarks